United States Patent [19]

Smith

[11] Patent Number: 5,750,339
[45] Date of Patent: May 12, 1998

[54] METHODS FOR IDENTIFYING FETAL CELLS

[75] Inventor: J. Bruce Smith, Philadelphia, Pa.

[73] Assignee: Thomas Jefferson University, Philadelphia, Pa.

[21] Appl. No.: 347,506

[22] Filed: Nov. 30, 1994

[51] Int. Cl.$^6$ .............................. C12Q 1/68; G01N 33/53
[52] U.S. Cl. ................................................ 435/6; 435/7.21
[58] Field of Search ................... 435/7.21, 6; 536/24.31

[56] References Cited

U.S. PATENT DOCUMENTS

| | | | |
|---|---|---|---|
| 4,551,435 | 11/1985 | Liberti et al. | 436/541 |
| 4,795,698 | 1/1989 | Owen et al. | 435/4 |
| 5,108,933 | 4/1992 | Liberti et al. | 436/501 |
| 5,153,117 | 10/1992 | Simons | 435/2 |
| 5,186,827 | 2/1993 | Liberti et al. | 210/222 |
| 5,200,084 | 4/1993 | Liberti et al. | 210/695 |

FOREIGN PATENT DOCUMENTS

| | | |
|---|---|---|
| WO86/06170 | 10/1986 | WIPO. |
| WO 91/07660 | 5/1991 | WIPO. |
| WO91/07660 | 5/1991 | WIPO. |
| WO 94/02646 | 2/1994 | WIPO. |
| WO94/15696 | 7/1994 | WIPO. |

OTHER PUBLICATIONS

Yelavarthi, Krishna, et al., Analysis of HLA–G mRNA in Human Placental and Extraplacental Membrane Cells BY In Situ Hybridization, J. Immunol. 146: 2847–2854, May 15, 1991.
Moreau, P., et. al, HLA–G mRNA Forms in Human Trophoblasts and Peripheral Blood Lymphocytes, Folia Biologica 40: 431–438, 1994.
Holzgreve, et. al., Fetal Cells in Maternal Circulation, J. Reprod. Med., 37(5):410–418, May 1992.
Moreau et al., "HLA–G mRNA forms in human trophoblasts and peripheral blood lymphocytes: Potential use in prenatal diagnosis," *Folia Biologica* 1994, 40(6): 431–438.
Busch, J., "Enrichment of Fetal Cells from Maternal Blood by High Gradient Magnetic Cell Sorting (Double MACS) for PCR–Based Genetic Analysis", *Prenatal Diagnosis* 1994, 14, 1129–1140.
Ganshirt–Ahlert, D. et al., "Detection of Fetal Trisomies 21 and 18 From Maternal Blood Using Triple Gradient and Magnetic Cell Sorting", *American J. of Reproductive Immunology* 1993, 30, 194–201.
Van Wijk, I. et al., "Multiparameter In Situ Analysis of Trophoblast Cells in Mixed Cell Populations by Combined DNA and RNA In Situ Hybridization", *J. Of Histochemistry and Cytochemistry* 1995, 43(7), 709–714.
Yagel, S. et al., Trophoblasts Circulating in Maternal Blood as Candidates for Prenatal Genetic Evaluation, *Human Reproduction* 1994, 9(6), 1184–1189.
Bianchi, D.W., et al., "Isolation of Fetal DNA from Nucleated Erythrocytes in Maternal Blood" *Proc.Natl.Acad.Sci. USA* 87:3279–3283, 1990.

Chumbley, G. "In Situ Hybridization and Northern Blot Demonstration of HLA–G mRNA in Human Trophoblast Populations by Locus–Specific Oligonucleotide" Human Immunology 37: 17–22 (1993).
Ellis, S. et al., "HLA G: At the Interface" *Am.J.Reprod.Immunol.* 23:84–86, 1990.
Ellis, S. et al., "Human Trophoblast and the Choriocarcinoma Cell Line BeWo Express a Truncated HLA Class I Molecule" *J.Immunol.* 144:731–735, 1990.
Geraghty, D.E. et al., "A Human Major Histocompatibility Complex Class I Gene That Encodes a Protein with a Shortened Cytoplasmic Segment" Proc. Natl. Acad. Sci. USA 84:9145–9149 (1987).
Grabowska, A., et al., "Human Trophoblast Cells in Culture Express an Unusual Major Histocompatibility Complex Class I–Like Antigen" American J. of Reproductive Immunology 23: 10–18 (1990).
Haynes, Mark K. et al., "Cytokine Production in First Trimester Chorionic Villi: Detection of mRNAs and Protein Products in Situ" *Cell.Immunol.* 151:300–308, 1993.
Kirszenbaum et al.,, "An Alternatively Spliced Form of HLA–G mRNA in Human Trophoblasts and Evidence for the Presence of HLA–G Transcript in Adult Lymphocytes" Proc. Acad. Natl. Sci. USA 91:4209–4213 (1994).
Kovats, S et al., "A Class I Antigen, HLA–G, Expressed in Human Trophoblasts" *Science* 248:220–223, 1990.
Lata, J. et al., "Localization of Major Histocompatiility Complex Class I and II mRNA in Human First–Trimester Chorionic Vill by In Situ Hybridization", *J.Exp.Med.* 175:1027–1032, 1992.
Lo, Cecilia W., "Localization of Low Abundance DNA Sequences in Tissue Sections by in Situ Hybridization" *J.Cell.Sci.* 81:143–162, 1986.
Odum, Niels et al., "Homotypic Aggregation of Human Cell Lines by HLA Class II, Class Ia–and HLA–G–Specific Monoclonal Antibodies" Eur. J. Immunol. 21:2121–2131 (1991).
Price, et al., "Prenatal Diagnosis with Fetal Cells Isolated from Maternal Blood by Multiparameter Flow Cytometry", *Am. J.Obstet.Gynecol.* 165:1731–1737, 1991.
Risk, JM et al., "Northern Blot Analysis of HLA–G Expression by BeWo Human Choriocarcinoma Cells" *J.Reprod.Immunol.* 18:199–203, 1990.

(List continued on next page.)

*Primary Examiner*—Eggerton A. Campbell
*Attorney, Agent, or Firm*—Law Offices of Jane Massey Licata

[57] ABSTRACT

The invention features a method of distinguishing fetal cells from maternal cells in a sample. The method comprises the steps of contacting a sample comprising fetal cells and maternal cells with a probe which is complementary to HLA-G mRNA and identifying individual cells in which the probe hybridize to mRNA in the cells. The absence of hybridization indicates that the cells are maternal cells. The presence of hybridization indicates that the cells are fetal cells. Fetal cells identified in accordance with the invention may be tested for genetic abnormalities.

17 Claims, No Drawings

OTHER PUBLICATIONS

Sanders, SK, et al., "Cell—Cell Adhesion Mediated by CD8 and Human Histocompatibility Leukocyte Antigen G, a Nonclassical Major Histocompatibility Complex Class 1 Molecule on Cytotrophoblasts" *J. Exp. Med.* 174: 737–740 (1991).

Shorter, S.C. et al., "Antigenic Heterogeneity of Human Cytotrophoblast and Evidence for the Transient Expression of MHC Class I Antigens Distinct from HLA–G" *Placenta* 14: 571–582 (1993).

Shukla, H et al., "The mRNA of a Human Class I Gene HLA G/HLA 6.0 Exhibits a Restricted Pattern of Expression" *Nucleic Acids Res.* 18: 2189 1990.

Tuan et al., "Histochemical Localization of Gene Expression in *Onchocerca volvulus*: in Situ DNA Histohybridization and Immunocytochemistry" *Mol.Biochem.Parasit.* 49:191–204, 1991.

Wachtel, S., et al., "Fetal Cells in the Maternal Circulation: Isolation by Multiparameter Flow Cytometry and Confirmation by Polymerase Chain Reaction" *Hum.Reprod.* 6:1466–1469, 1991.

Wei, X. and Orr, H.T., "Differential Expression of HLA–E, HLA–F, and HLA–G Transcripts in Human Tissue" *Hum.Immunol.* 29:131–142, 1990.

Yelavarthi, K.K. et al., "Analysis of HLA–G mRNA In Human Placental And Extraplacental Membrane Cells by in Situ Hybridization" *J.Immunol.* 146:2847–2854, 1991.

Yelavarthi, KK et al., "Cellular Distributionof HLA–G mRNA in Transgenic Mouse Placentas" *J. of Immunology* 151: 3638–3645 (1993).

METHODS FOR IDENTIFYING FETAL CELLS

ACKNOWLEDGEMENT OF U.S. GOVERNMENT RIGHTS

The invention was made in part with U.S. Government funds (NIH, NICHD, Grant No. NO1-HD-4-3201) and the U.S. Government may have certain rights in the invention.

FIELD OF THE INVENTION

The invention relates to methods of identifying fetal cells in a sample which contains fetal cells and maternal cells.

BACKGROUND OF THE INVENTION

HLA-G, a member of the non-classical HLA class I genes of the human major histocompatibility complex, encodes a nonpolymorphic antigen expressed in placental and some fetal tissues. This fetus-specific histocompatibility gene is expressed in placental extravillous membranes and in trophoblasts, but has not been found in fetal thymus, skin, and liver. HLA-G specific mRNA has also been found in fetal eye tissues (Shukla et al., *Nucleic Acids Res.* 18:2189, 1990). HLA-G is not expressed in adult T cells, T cell blasts and several human T and B cell tissue culture lines (Wei et al., *Hum.Immunol.* 29:131–142, 1990). However, expression of this gene has been demonstrated in the human choriocarcinoma cell lines JEG and BeWo (Risk et al., *J. Reprod.Immunol.* 18:199–203, 1990; Ellis et al., *J. Immunol.* 144:731–735, 1990; Ellis et al., *Am.J.Reprod.Immunol.* 23:84–86, 1990) and in first trimester chorionic villi (Yelavarthi et al., *J.Immunol.* 146:2847–2854, 1991; Lata et al., *J.Exp.Med.* 175:1027–1032, 1992). Expression of HLA-G in trophoblasts decreases during the course of pregnancy and is greatly reduced in the third trimester compared with the first trimester (Kovats et al., *Science* 248:220–223, 1990). While low levels of an alternatively spliced form of HLA-G have been found in adult lymphocytes (Kirszenbaum et al., 1994, Proc. Acad. Natl. Sci. USA 91:4209–4213), expression of HLA-G per se is limited to only a few tissues in the fetus and placenta.

Assessment of fetal development (prenatal diagnosis) is generally conducted by analysis of fetal cells for genetic abnormalities. Procedures for obtaining fetal cells include chorion villus sampling (CVS) and amniocentesis, both of which are termed invasive medical procedures and which have an associated risk of spontaneous miscarriage of less than 1%. There is a long felt need for an non-invasive method of obtaining fetal cells for genetic analysis and for distinguishing these fetal cells from non-fetal cells.

SUMMARY OF THE INVENTION

The invention features a method of distinguishing fetal cells from maternal cells in a sample comprising fetal cells and maternal cells. The method comprises the steps of (a) contacting a sample comprising fetal cells and maternal cells with a probe; the probe being a nucleic acid molecule comprising a nucleotide sequence complementary to the nucleotide sequence of HLA-G mRNA; and, (b) identifying cells in which the probe hybridizes to mRNA in the cells; wherein the absence of hybridization of the probe to mRNA in the cells is an indication that the cells are maternal cells and the presence of hybridization of the probe to mRNA in the cells is an indication that the cells are fetal cells.

In one aspect of the invention, the method comprises isolating the fetal cells from the sample. In another aspect, the sample is maternal blood, mucous from the maternal cervix or mucous from the maternal vagina. Preferably, the sample is maternal blood.

In yet another aspect of the invention, the method comprises the step of removing non-mononuclear cells from the sample prior to contacting the cells with the probe. In another aspect, maternal cells are depleted from the sample prior to contacting the cells with the probe. In yet another aspect, fetal cells are enriched in the sample prior to contacting the cells with the probe. In addition, in another aspect, maternal cells are depleted from the sample and fetal cells are enriched in the sample prior to contacting the cells with the probe.

According to the methods of the invention, depletion of maternal cells is effected by the steps of incubating the cells in the presence of anti-maternal antibody, f u r t h e r incubation the cells in the presence of anti-anti-maternal antibody, the anti-anti-maternal antibody being conjugated to iron, and removing cells to which the anti-maternal antibody and the anti-anti-maternal antibody are bound using a magnetic separator. In some embodiments, the anti-maternal antibody is murine antibody. Preferably, the anti-maternal antibody is selected from the group consisting of anti-human CD14, anti-human CD4, anti-human CD8, anti-human CD3, anti-human CD19, anti-human CD32, anti-human CD16 and anti-human CD45. Also preferably, the anti-anti-maternal antibody is goat anti-murine antibody.

According to the methods of the invention, enrichment of fetal cells is effected by incubating the cells in the presence of anti-fetal antibody, further incubating the cells in the presence of anti-anti-fetal antibody, the anti-anti-fetal antibody being conjugated to iron, and recovering cells to which the anti-fetal antibody and the anti-anti-fetal antibody are bound using a magnetic separator.

Preferably, the anti-fetal antibody is murine antibody. More preferably, the anti-fetal antibody is selected from the group consisting of anti-human CD71, anti-human CD36 and anti-human glycophorin A. Also preferably, the anti-anti-fetal antibody is goat anti-mouse antibody.

Further, according to the methods of the invention, the probe comprises a portion of the nucleotide sequence complementary to the nucleotide sequence of mRNA encoding HLA-G, wherein said portion hybridizes to said mRNA but does not hybridize to MRNA encoding classical class I HLA antigen.

The invention also features a method of detecting a genetic abnormality in a fetus comprising the steps of (a) contacting a sample comprising fetal cells and maternal cells with a probe; the probe being a nucleic acid molecule comprising a nucleotide sequence complementary to the nucleotide sequence of HLA-G mRNA; (b) isolating cells in which the probe hybridizes to mRNA in the cells, and (c) testing the cells for the presence of the genetic abnormality.

Preferably, the abnormality is selected from the group consisting of trisomy 21, trisomy 13, trisomy 14, trisomy 15, trisomy 16, trisomy 18, trisomy 22, triploidy, tetraploidy, chromosome deletions, sex chromosome abnormalities such as XO, XXY, XYY, XXX, Tay Sachs disease, mucopolysaccharidoses, cystic fibrosis, Duchenne muscular dystrophy, Hemophilia A, β-thalassemia, sickle cell anemia, phenylketonuria and Gaucher disease.

DETAILED DESCRIPTION

The invention features methods of distinguishing fetal cells from non-fetal cells, particularly maternal cells in a sample containing both fetal cells and non-fetal cells.

According to the present invention, fetal cells can be identified in and, in some embodiments, isolated from a sample containing maternal cells and fetal cells. The fetal cells, when so identified, may be used in a genetic analysis of the fetus to assess the health of the fetus. In particular, the methods of the invention include the use of HLA-G as a marker to identify fetal cells in a sample containing maternal cells and fetal cells. The methods of the invention may be used as non-invasive methods for identifying fetal cells in samples taken from pregnant women, which methods reduce the risk to both mother and fetus while providing the means to obtain material from the fetus which can be analyzed for genetic defects and/or disorders. The invention is particularly useful in the identification of fetal cells in maternal blood. Thus, the methods of the invention facilitate performance of prenatal diagnosis particularly during the first trimester of pregnancy, and because the methods of the invention rely on tests performed on samples obtained using relatively non-invasive procedures, they are safer for both the mother and fetus than traditional chorion villus sampling and amniocentesis.

The methods of the invention are based on the discovery that expression of HLA-G unambiguously identifies cells of fetal origin in maternal blood and can therefore be used as a marker for fetal cells which are present in low amounts in maternal blood. By "maternal blood" is meant blood obtained from a pregnant mother. It is estimated that nucleated fetal cells are present in maternal blood during the first trimester of pregnancy at a concentration of 1–10 per 10 million maternal mononuclear blood cells. Currently available markers useful for identification of fetal cells in a population of fetal and maternal cells include those capable of identifying male but not female fetal cells, and those which detect chromosome abnormalities present in fetal cells but not maternal cells. Thus, there has been a long felt need for the development of a marker which simply identifies fetal cells in maternal blood, irrespective of gender or the presence or absence of chromosomal abnormalities, which cells when so identified, may be examined to determine the health of the developing fetus. Expression of the HLA-G gene provides such a marker. Once a population of cells in maternal blood is identified as being fetal, techniques and probes for identifying aneuploidy of somatic and sex chromosomes, and for identification of specific genes are readily available in the art.

According to the methods of the invention, identification of fetal cells is based on expression by the fetal cells of HLA-G. To distinguish fetal cells from maternal cells, expression of HLA-G may be assessed directly in a sample of fetal and maternal cells. In preferred embodiments, maternal cells may be depleted from a sample containing fetal cells and maternal cells, or fetal cells may be enriched from a sample containing fetal cells and maternal cells, or, both depletion of maternal cells and enrichment of fetal cells may be conducted. Expression of HLA-G in cells of the sample identifies such cells in the sample as being fetal cells. Once identified, fetal cells may be analyzed in the sample and/or isolated from the sample.

According to the methods of the invention, a sample is provided which contains fetal cells mixed with maternal cells. The sample may be maternal blood, or mucous obtained from the cervix or vagina of the mother during the early stage of pregnancy. Fetal cells contained in a sample obtained from the cervix or vagina of the mother are likely to be trophoblasts which are shed from the developing placenta. Such trophoblasts can be differentiated from epithelial cells and maternal leukocytes using techniques known in the art. Preferably, the sample is maternal blood. The amount of maternal blood is preferably 0.01 ml to 50 ml, containing approximately $10^4$–$10^8$ cells. The sample is obtained from the pregnant woman using routine procedures available in the art.

In some preferred embodiments, prior to identifying fetal cells in a sample of fetal and maternal cells, the sample is processed to eliminate non-mononucleated cells. Since the fetal cells of interest are mononucleated, the elimination of non-mononucleated cells from the sample effectively increases the concentration of fetal cells in the sample. If the sample is a blood sample, elimination of non-mononucleated cells removes maternal red blood cells which comprise the vast majority of the cells in the sample. Methods of isolating mononucleated cells and of elimination of non-mononucleated cells are well know in the art and include, among others, ficoll hypaque centrifugation, or lysis of mature red blood cells using water, bicarbonate or tris-buffered ammonium chloride.

In some preferred embodiments, prior to identifying fetal cells, the maternal cells in the sample are depleted to reduce their number relative to the number of fetal cells. As used herein, the term "maternal cell surface antigens" is meant to refer to cell surface antigens which are found on maternal cells but which are not found on fetal cells or are found infrequently on fetal cells. Examples of maternal cell surface antigens useful in the invention include but are not limited to CD14, CD4, CD8, CD3, CD19 and CD45.

Cells which express maternal cell surface antigens may be selectively removed from a sample using several different techniques known in the art including flow cytometry, affinity chromatography and/or magnetic separation techniques. Examples of methods and apparatuses useful for selectively removing cells which contain maternal cell surface antigens from a sample are described in U.S. Pat. Nos. 5,200,084 and 5,186,827, and in patent application Ser. No. WO9415696, each of which is herein incorporated by reference.

According to some embodiments, cells which contain maternal cell surface antigens may be selectively removed using magnetic separation technology. In some embodiments, a sample is first contacted with antibodies which bind to maternal cell surface antigens, also referred to herein as anti-maternal antibodies. Antibodies which bind to anti-maternal antibodies, referred to herein as anti-anti-maternal antibodies are then added. Anti-anti-maternal antibodies are conjugated to iron. A magnetic separator is used to isolate cells which have associated with them maternal cell surface antigen. This is accomplished by isolating, from the mixture which includes the sample, cells which have bound to them anti-maternal antibodies and anti-anti-maternal antibodies conjugated to iron. The isolated cells are discarded and the remaining cells constitute a sample which is depleted of maternal cells. In some embodiments, the anti-maternal antibody is at least one antibody selected from the group consisting of murine anti-human CD14, CD4, CD8, CD3, CD19, CD32, CD16 and CD45 antibody, and the anti-anti-maternal antibody is a goat anti-murine antibody.

In some embodiments, a single anti-maternal antibody is used to deplete the maternal cells in a sample. In other embodiments, two or more anti-maternal antibodies are used to deplete the maternal cells in a sample. In embodiments in which two or more anti-maternal antibodies are used to deplete the maternal cells in a sample, the cells are contacted with multiple anti-maternal antibodies in a single step. In other embodiments in which two or more anti-maternal antibodies are used to deplete the maternal cells in a sample, the cells are contacted with multiple anti-maternal antibodies in sequential steps. In yet other embodiments in which two or more anti-maternal antibodies are used to deplete the maternal cells in a sample, the cells are contacted with one or more anti-maternal antibodies in a single step, followed by another step in which the cells are further contacted with one or more anti-maternal antibodies.

Selective enrichment of fetal cells in maternal blood facilitates their identification and isolation. This is accomplished by enriching fetal cells using antibodies to cell surface molecules, which molecules are expressed only on fetal cells, using a variety of magnetic or flow cytometry selection techniques. Techniques and apparatus for separation of cells using magnetic properties are known in the art and are described in U.S. Pat. Nos. 5,200,084 and 5,186,827, and in patent application Ser. No. WO9415696, each of which is herein incorporated by reference. The concentration of fetal cells in a sample may be increased relative to the number of maternal cells by selectively removing cells which do not contain cell surface antigens that are found on fetal cells. As used herein, the term "fetal cell surface antigens" is meant to refer to cell surface antigens that are found on fetal cells. Examples of fetal cell surface antigens include CD71 (transferase receptor protein), CD36 and glycophorin A. CD34, an antigen found only on stem cells, may also be useful in the methods of the invention.

In some embodiments, a sample is first contacted with antibodies which bind to the fetal cell surface antigens, also referred to herein as anti-fetal antibodies. Antibodies which bind to the anti-fetal antibodies, referred to herein as anti-anti-fetal antibodies are added. The anti-anti-fetal antibody is conjugated to iron. A magnetic separator is used to isolate cells which have associated with them fetal cell surface antigen. This is accomplished by isolating, from the mixture which includes the sample, cells which have bound to them anti-fetal antibodies and anti-anti-fetal antibodies conjugated to iron. The isolated cells, constituting a sample enriched for fetal cells, are retained and the remaining cells are discarded. In some embodiments, the anti-fetal antibody is murine anti-human CD71 antibody, murin anti-human CD36 antibody or murine anti-human glycophorin A antibody and the anti-anti-fetal antibody is goat anti-murine antibody.

In some embodiments of the invention, maternal cells are depleted from the sample prior to identifying fetal cells. In other embodiments, fetal cells are enriched in the sample prior to identifying fetal cells. In yet other embodiments, maternal cells are depleted from and fetal cells are enriched in the sample prior to identifying fetal cells. In yet other embodiments, fetal cells are identified in the sample in the absence of depletion of maternal cells or enrichment of fetal cells.

The means for enriching fetal cells in maternal blood are not limited to the methods described above. Rather, other means may be used, for example, the methods for isolating fetal cells from maternal blood described in patent application Ser. No. WO 91/07660 may also be used. These methods include separation of fetal cells from maternal cells using antibodies such as anti-transferrin antibody and anti HLe-1 (anti-CD45) antibody coupled to cell separation techniques such as cell panning, flow cytometry and/or magnetic separation techniques.

The probes used to identify fetal cells in a sample containing fetal and maternal cells include nucleic acid molecules which comprise the nucleotide sequence complementary to the nucleotide sequence of mRNA encoding HLA-G, or which comprise a portion of the nucleotide sequence complementary to the nucleotide sequence of mRNA encoding HLA-G, such a portion consisting of a nucleotide sequence sufficient to effect hybridization of the probe to HLA-G in the absence of cross hybridization of the probe to classical class I HLA antigens. The probe is preferably labelled. In some embodiments, the probe is labelled with a radioactive marker and in other embodiments, the probe is labelled with a non-radioactive marker, for example, biotin. Preferably, the probe is labelled with biotin and the method for detecting fetal cells in the sample is in situ hybridization.

Other probes useful to distinguish, identify, isolate the fetal cells from maternal cells include antibodies specific for HLA-G. Anti-HLA-G monoclonal antibody is disclosed in Odum et al. (1991, Eur. J. Immunol. 21:2121–2131).

The means for detecting expression of HLA-G in fetal cells are not limited to the use of biotinylated probes in in situ hybridization. Other methods for detection of expression of HLA-G in fetal cells may also be used. These methods include use of an HLA-G probe which is radiolabelled, or which is labelled with a non-radioactive compound other than biotin in in situ hybridization experiments. Fetal cells may also be identified through the use of in situ PCR technology using primers specific for amplification of HLA-G specific mRNA. Nucleic acid may be extracted from fetal cells and Northern blot hybridization or PCR may be performed to identify HLA-G specific mRNA. HLA-G specific antibodies may also be used to identify fetal cells expressing HLA-G either within or on the surface of the cells. Further, an HLA-G probe which is smaller than the full length of the cDNA encoding HLA-G may be used provided that such a probe does not appreciably cross-hybridize with other HLA-specific nucleic acids thereby resulting in false positive identification of fetal cells.

HLA-G serves as an independent marker for fetal nucleated cells and thus facilitates their differentiation from adult cells in maternal blood. Since present technology for identification of fetal cells in a population of adult cells relies on the demonstration of male cells in female blood or the presence of fetal or embryonic hemoglobins that are not expressed by adult cells, use of the methods of the invention employing HLA-G provides significant advantages over present methods. Further, although antibodies which react with trophoblasts have been reported, many such antibodies cross react with adult (maternal) cells and therefore do not provide reliable identification of fetal cells in maternal blood. Since examination of fetal cells by chorion villus sampling or amniocentesis incurs the risk of spontaneous miscarriage, use of HLA-G as a marker for fetal cells in maternal blood provides a relatively non-invasive procedure for accurate assessment of the health of the developing fetus. Fetal cells so identified may then be tested, using procedures known in the art, to determine whether or not they exhibit characteristics of any one of a variety of disease states.

In addition to serving as an independent fetal cell marker, reagents which specifically react with HLA-G, including cDNA probes or antibodies to unique cell surface determinants encoded by the HLA-G gene, are useful as tools for purifying fetal cells from maternal blood. For example, a population of cells may be incubated in the presence of a biotinylated cDNA probe specific for HLA-G mRNA. Cells may be further incubated in the presence of avidin conjugated to iron or anti-biotin antibody conjugated to iron. Cells to which the probe has bound will also bind avidin or anti-biotin antibody and may be thus identified and/or separated from the population using a magnetic separator.

In addition, reverse-transcriptase polymerase chain reaction (RT-PCR) specific for HLA-G mRNA could be used to quantitate fetal cells in maternal blood. Quantitative reverse transcriptase-PCR is known in the art. The number of fetal cells in a population of cells whose total number is known may be estimated by comparing the quantity of mRNA specific for HLA-G in the cell population to the quantity of mRNA specific for classical class I HLA antigens in same cell population. Assuming that each cell expresses approximately the same amount of classical class I HLA specific mRNA, the number of fetal cells in the population may be estimated from the amount of HLA-G specific mRNA present in the population. Diseases which can be detected in the fetus, by examination of fetal cells obtained following the methods of the invention, include all diseases for which there is a characteristic karyotype, including diseases associated with aneuploidy such as Down Syndrome (trisomy 21) and other trisomies (usually 13, 14, 15, 16, 18, or 22). Other diseases include those associated with the presence of extra sets of chromosomes (triploidy or tetraploidy), those associated with deletions of part of a chromosome, those associated with sex chromosome abnormalities (XO, XXY, XYY, XXX), and those associated with balanced and unbalanced rearrangements of chromosomes, such as translocations. Diseases which are associated with chromosome breaks include Fanconi's anemia, Bloom's syndrome and Ataxia telangiectasia. Diseases which may also be detected in the fetus include those which can be diagnosed by protein/enzyme abnormalities such as but not limited to, Tay Sachs disease and the mucopolysaccharidoses. In addition, single gene disorders may be diagnosed. Upon identification of the gene in question, restriction fragment length polymorphism analysis or PCR analysis can be conducted to diagnose cystic fibrosis, Duchenne muscular dystrophy, Hemophilia A, β-thalassemia, sickle cell anemia, phenylketonuria, Gaucher disease, Severe Combined Immunodeficiency Disorder, and any other disease for which a probe, an enzyme or a cell surface marker is known. All of the above named conditions and the associated chromosome or enzyme abnormalities are known in the art as are methods of detecting these diseases. In fact, the methods of the invention may be used to detect any disease in a fetus for which a gene, a probe, a chromosome abnormality or an enzyme abnormality is known.

EXAMPLE 1

To effect isolation of fetal cells in maternal blood, maternal cells are first depleted from the sample. This is accomplished by separating mononuclear cells (MNCs) from maternal peripheral venous blood (usually 20 ml) by standard ficoll hypaque centrifugation. Maternal MNC are then depleted from the sample by first adding to the sample of cells a series of mouse anti-human antibodies. Antibodies typically employed are commercially available and may include those to CD14 (monocytes), CD4 and CD8 (T cells), CD3 (T cells), CD19 (B cells), CD32 and CD16 (granulocytes) and CD45 (leukocytes in general). Next, goat anti-mouse antibodies are added to the sample, which antibodies are conjugated to iron (Ferrofluid, Immunicon). Cells with bound antibodies are separated from cells without bound antibodies using a magnetic cell separator (Immunicon Corp.). Those cells with antibodies bound to them will be retained on magnetized wire loops or surfaces in the magnetic cell separator. This procedure, results in depletion of as much as 99% or more of adult MNC.

In general, either separately or sequentially, mononuclear cells are incubated with 20 µl of commercially available monoclonal antibody for 30–45 minutes on ice. The cells are then reincubated with Ferrofluid (the stock solution is diluted 1:40–1:100 in physiological solution), washed, and then "pulled" to wire loops which have been magnetized in a device which generates a high gradient magnetic field (Immunicon magnetic cell separator) . The monoclonal antibodies are used as prepared by the suppliers. The combination of antibodies used is preferably CD14 and CD45, or CD14, CD4, CD8, CD32, CD16 and CD19.

When depletion of maternal cells is complete, positive selection of fetal cells in the sample is accomplished using a magnetic cell separator, ferrofluid and antibodies to CD71, CD36 or glycophorin A. CD71 is the transferrin receptor which is expressed abundantly on fetal nucleated red blood cells. Generally, cells remaining following depletion are incubated in the presence of 20 µl of anti-CD71 or anti-glycophorin A (a red cell marker expressed to high levels on fetal erythrocytes and their precursor cells) or with a combination of both antibodies. Following 30–45 minutes on ice , Ferrofluid is added and the cells are positively selected onto magnetized wire loops. These cells are washed in the magnetic field and then are recovered from the wire loops following removal of the magnetic field.

Messenger RNA specific for HLA-G is detected by in situ cDNA-mRNA hybridization following published methodology (Lo, *J.Cell.Sci.* 81:143–162, 1986; Tuan et al., *Mol.Biochem.Parasit.* 49:191–204, 1991; Haynes et al., *Cell.Immunol.* 151:300–308, 1993). A cDNA probe specific for HLA-G useful for demonstrating expression of HLA-G in first trimester trophoblast is used (Lata et al., *J.Exp.Med.* 175:1027–1032, 1992). Essentially, target tissue is incubated in the presence of biotinylated cDNA probe under conditions suitable for hybridization of the probe to HLA-G mRNA. The sequence of the HLA-G cDNA probe is disclosed in Geraghty et al. (1987, Proc. Natl. Acad. Sci. USA 84:9145–9149) which is herein incorporated by reference. The hybridized probe is then visualized by reaction with streptavidin-alkaline phosphatase and chromogenic substrate. Examination of nucleated cells in fetal peripheral blood revealed that HLA-G mRNA is present in 100% of these cells at 10–12 weeks gestation and that the percentage of HLA-G positive cells decreased to about 60% by 20 weeks gestation. These results are presented below.

TABLE 1

| Marker | Fetal Blood MNC | Adult Peripheral Blood MNC |
|---|---|---|
| 12 Week Fetal Blood | | |
| *Bluescript | Neg. | Neg. (Few Cells) |
| HLA-Class I (B7) | Neg. | Str. Pos. (All cells) |
| β-2 Microglobulin | Neg. (Occas. Wk. +) | Pos. (Few Cells) |
| HLA-DRB | Neg. | No Cells Seen |
| HLA-G | Str. Pos. (All Cells) | Neg. |
| 20 Week Fetal Blood | | |
| *Bluescript | Neg. | Neg. |
| HLA-Class I (B7) | 25% Positive | 100% Positive |
| HLA-G | 60% Positive | Neg. |

*Bluescript represents the control probe used.

These data suggest a possible inverse relationship between expression of classical MHC genes and HLA-G. Cells positive for HLA-G mRNA were also found in blood obtained from the intervillous space.

EXAMPLE 2

To determine which types of fetal peripheral blood cells might enter the intervillous space and the maternal circulation, flow cytometry was performed on samples of 12 week fetal blood. In two separate experiments greater than 90% of fetal nucleated peripheral blood cells expressed high levels of transferrin receptor (CD71) and less than 5% of these cells were positive for the general leukocyte marker CD45. The latter result is clone dependent, in that up to 20% of fetal cells reacted with clone J.33 (Beckton-Dickinson) and clone ALB- 12 (Amac) providing data indicating the <5% are positive for CD45 (the CD45 molecule has a number of distinct antigenic epitopes and the antibodies to these epitopes are not necessarily cross-reactive).

These data are consistent with the results of experiments determining the phenotypes of cells in matched intervillous space (IVS) and maternal peripheral blood. The results of two such experiments in which limited phenotyping was completed on matched samples are given below.

TABLE 2

Phenotypes of IVS and peripheral blood mononuclear cells by flow cytometry*.

| Marker** | Experiment 1 | | Experiment 2 | |
| --- | --- | --- | --- | --- |
| | Ivs | Blood | Ivs | Blood |
| CD2 | 17.41% | 70.08% | 16.30% | 77.30% |
| TCRαβ | 16.97 | 66.63 | 13.22 | 71.88 |
| TCRγδ | 0.86 | 2.30 | 0.08 | 1.97 |
| GLY-A | ND | ND | 72.00 | 2.70 |
| CD56+16+ | 0.74 | 12.61 | 2.65 | 16.62 |
| CD8 | 10.44 | 19.79 | 6.03 | 34.37 |
| CD4 | 6.87 | 50.49 | 6.49 | 38.36 |

*Gates were set on the CD45+ population of leukocytee in each sample.
*Data are presented as % of gated cells.
**TCR = T cell receptor Since there are clear physiologic or mechanical reasons why fetal blood cells enter the maternal circulation during normal pregnancy (Bianchi, D.W., et al., Proc.Natl.Acad.Sci. USA 87:3279–3283, 1990, Wachtel, S., et al., Hum.Reprod. 6:1466–1469, 1991, Price, et al., Am. J.Obstet.Gynecol. 165:1731–1737, 1991), it is likely that these results reflect natural movement of fetal cells into the maternal blood during pregnancy rather than movement caused by bleeding into the IVS from severed vessels in the villi during the experimental procedure.

What is claimed is:

1. A method of distinguishing nucleated fetal cells from maternal cells in a sample comprising maternal blood containing nucleated fetal cells and maternal cells, said method comprising:

(a) contacting a sample comprising maternal blood containing nucleated fetal cells and maternal cells with a probe; said probe being a nucleic acid molecule comprising a nucleotide sequence complementary to the nucleotide sequence of HLA-G mRNA; and (b) identifying cells in which said probe hybridizes to mRNA in said cells; wherein the absence of hybridization of said probe to mRNA in said cells is an indication that said cells are maternal cells and the presence of hybridization of said probe to mRNA in said cells is an indication that said cells are nucleated fetal cells.

2. The method of claim 1 further comprising isolating said fetal cells from said sample.

3. The method of claim 1 further comprising the step of removing non-mononuclear cells from said sample prior to contacting said cells with said probe.

4. The method of claim 1, wherein maternal cells are depleted from said sample prior to contacting said cells with said probe.

5. The method of claim 1, wherein fetal cells are enriched in said sample prior to contacting said cells with said probe.

6. The method of claim 3, wherein maternal cells are depleted from said sample and fetal cells are enriched in said sample prior to contacting said cells with said probe.

7. The method of claim 4, wherein said depletion of maternal cells is effected by the steps of incubating said cells in the presence of anti-maternal antibody, further incubation said cells in the presence of anti-anti-maternal antibody, wherein said anti-anti-maternal antibody is conjugated to iron, and removing cells to which said anti-maternal antibody and said anti-anti-maternal antibody are bound using a magnetic separator.

8. The method of claim 7, wherein said anti-maternal antibody is murine antibody.

9. The method of claim 8, wherein said murine antibody is selected from the group consisting of anti-human CD14, anti-human CD4, anti-human CD8, anti-human CD3, anti-human CD19, human anti-CD32, human anti-CD16 and anti-human CD45.

10. The method of claim 7, wherein said anti-anti-maternal antibody is goat anti-murine antibody.

11. The method of claim 5, wherein said enrichment of said fetal cells is effected by incubating said cells in the presence of anti-fetal antibody, further incubating said cells in the presence of anti-anti-fetal antibody, wherein said anti-anti-fetal antibody is conjugated to iron, and recovering cells to which said anti-fetal antibody and said anti-anti-fetal antibody are bound using a magnetic separator.

12. The method of claim 11, wherein said anti-fetal antibody is murine antibody.

13. The method of claim 11, wherein said murine antibody is selected from the group consisting of anti-human CD71, anti-human CD36 and anti-human glycophorin A.

14. The method of claim 11, wherein said anti-anti-fetal antibody is goat anti-mouse antibody.

15. The method of claim 1, wherein said probe comprises a portion of the nucleotide sequence complementary to the nucleotide sequence of mRNA encoding HLA-G, wherein said portion hybridizes to said mRNA but does not hybridize to mRNA encoding classical class I HLA antigen.

16. A method of detecting a genetic abnormality in a fetus comprising (a) contacting a sample comprising maternal blood containing nucleated fetal cells and maternal cells with a probe; said probe being a nucleic acid molecule comprising a nucleotide sequence complementary to the nucleotide sequence of HLA-G mRNA;

(b) isolating cells in which said probe hybridizes to mRNA in said cells, and testing said cells for the presence of said genetic abnormality.

17. The method of claim 16, wherein said abnormality is selected from the group consisting of trisomy 21, trisomy 13, trisomy 14, trisomy 15, trisomy 16, trisomy 18, trisomy 22, triploidy, tetraploidy, chromosome deletions, chromosome translocations, chromosome breaks, sex chromosome abnormalities, Tay Sachs disease, mucopolysaccharidoses, cystic fibrosis, Duchenne muscular dystrophy, Hemophilia A, β-thalassemia, sickle cell anemia, phenylketonuria, Gaucher disease, Fanconi's anemia, Bloom's syndrome, Severe Combined Immunodeficiency Disorder and Ataxia telangiectasia.

* * * * *